United States Patent [19]

Holý et al.

[11] Patent Number: 4,605,658

[45] Date of Patent: Aug. 12, 1986

[54] ANTIVIRALLY ACTIVE ADENINE DERIVATIVES

[75] Inventors: Antonin Holý, Prague, Czechoslovakia; Erik de Clercq, Louvain, Belgium

[73] Assignees: Ceskoslovenska Akademie Ved., Prague, Czechoslovakia; Stichting Rega VZW, Louvain, Belgium

[21] Appl. No.: 658,438

[22] Filed: Oct. 5, 1984

[30] Foreign Application Priority Data

Oct. 7, 1983 [CS] Czechoslovakia ............... 7380-83

[51] Int. Cl.$^4$ ........................................... A61K 31/52
[52] U.S. Cl. .................................................... 514/261
[58] Field of Search .......................................... 514/261

[56] References Cited

U.S. PATENT DOCUMENTS 4,230,708  10/1980  De Clercq et al. ............... 424/253

FOREIGN PATENT DOCUMENTS

| 47-4077 | 2/1972 | Japan | 424/253 |
| 47-4078 | 2/1972 | Japan | 424/253 |
| 47-8549 | 3/1972 | Japan | 424/253 |
| 47-8550 | 3/1972 | Japan | 424/253 |

OTHER PUBLICATIONS

Holy et al., Collection Czechoslovak Chem. Commun., vol. 47, 1982, pp. 1392–1407.
De Clercq et al., Science, 200, 563 (1978).
Sodja et al., Acta Virol., 24, 317 (1980).
Rada et al., Chemotherapy, 26, 184 (1980).
Smee et al., Antimicrob. Ag. Chemother., 21, 66 (1982).
Kara et al., EEBS Letters 107, 187 (1979).
Votruba et al., Coll. Czech. Chem. Comm., 45, 3039 (1980).
De Clercq et al., Antivirol. Res., 3, 17 (1983).
Vince et al., J. Med. Chem., 20, 612 (1977).
Holy et al., Coll. Czech. Chem. Comm., 43, 3444 (1978).
Holy et al., Coll. Czech. Chem. Comm., 49, 2144 (1984).
De Clercq et al., "Journal of Medicinal Chemistry", vol. 22, No. 5, pp. 510–513 (1979).
De Clercq et al., "Journal of Medicinal Chemistry", vol. 28, No. 3, pp. 282–287 (1982).

*Primary Examiner*—Jerome D. Goldberg
*Attorney, Agent, or Firm*—Birch, Stewart, Kolasch & Birch

[57] ABSTRACT

Certain esters of 3-(adenin-9-yl)-2-hydroxypropanoic acid are disclosed which exhibit an improved broad spectrum antiviral activity while having a low toxicity for living cells. They can be used for treatment of virus diseases in human and veterinary practice.

20 Claims, No Drawings

ANTIVIRALLY ACTIVE ADENINE DERIVATIVES

This invention relates to chemical compounds which may be used in the treatment of virus diseases. More in particular, it relates to esters of 3-(adenin-9yl)-2-hydroxypropanoic acid, which exhibit a broad-spectrum antiviral activity and which can therefore be used with advantage in the treatment of diseases caused by RNA or DNA viruses.

It is known that certain adenine derivatives have antiviral properties. Thus, the compound 9-(2,3-dihydroxypropyl)adenine or DHPA has already been shown to exhibit a broad-spectrum antiviral activity in (S) or (RS) form while having a low acute toxicity for living cells (compare our U.S. Pat. No. 4,230,708 for further details).

In spite of this known matter, there is always a need for compounds showing similar or even better characteristics and a primary object of the invention is to provide chemical compounds having an improved antiviral activity.

A further object of the invention is to provide therapeutic compositions containing such antivirally active compounds and being useful for treating virus diseases in human and veterinary practice.

Another object is to provide a method of treating virus diseases which makes use of chemical compounds having an improved antiviral activity or therapeutic compositions containing the same.

In accordance with the present invention, there have now been found certain chemical compounds related to but distinct from DHPA, which exhibit, just like DHPA, a marked broad-spectrum antiviral activity while having a low toxicity for living cells. The level of their antiviral activity is higher than that of DHPA while their acute toxicity is of about the same level. This means that such compounds have improved antiviral properties over DHPA.

The compounds of the present invention are esters of 3-(adenin-9-yl)-2-hydroxypropanoic acid and can be represented by the general formula:

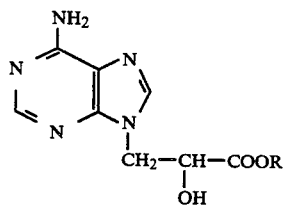

(I)

wherein R is a linear or branched $C_{1-5}$ alkyl group (with the exception of tert-butyl and n-pentyl) or an n-octyl, methoxyethyl or cyclohexyl group.

The esters of formula (I) can exist in (R) and (S) enantiomeric forms, dependent from the configuration of groups around the carbon atom in 2-position of the aliphatic side chain. Although it seems that the esters in (R) form are slightly better in antiviral activity than the corresponding esters in (S) form, both enantiomeric forms have improved characteristics and can be used with advantage in the treatment of virus diseases. The same applies to the racemic or (RS) form of the esters.

The esters of formula (I) differ from DHPA by the presence of an esterified carboxyl group instead of a hydroxyl group at the end of a 3-membered aliphatic side chain. This difference must be responsible for the improvement in antiviral properties although such effect could not be foreseen.

It should be noted that many derivatives related to DHPA are deprived of antiviral properties, compare De Clercq et al., J. Med. Chem., 197, Vol. 22, No. 5, pp. 510–513. A similar inactivity has been found for 3-(adenin-9-yl)-2-hydroxypropanoic acid. The fact that the esters of the present invention exhibit an improved activity in this field, must therefore be regarded as surprising.

Further, it should be noted that in DHPA only the S-enantiomeric form and the racemate are antivirally active, whilst the R-enantiomeric form is rather inactive. In the esters of the present invention, however, both the R and S enantiomeric forms have excellent antiviral activity.

Some compounds of general formula (I) have already been disclosed as potential agents for lowering the cholesterol level in blood, compare Japanese patent publications Nos. 72 04077 and 72 08548. Nevertheless, the antiviral activities of such compounds have not been disclosed before and seem to be novel in the art.

The compounds of formula (I) may be prepared by esterification of the corresponding free acids (formula II) with an alcohol ROH according to the following reaction scheme:

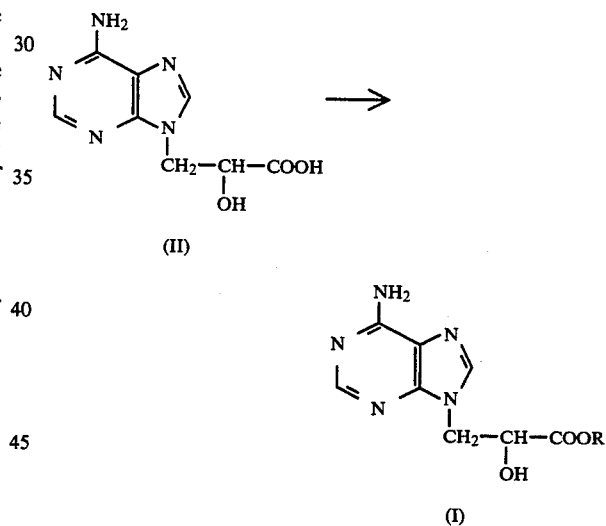

In this reaction scheme, R has the same meaning as indicated above.

If the starting material (II) is in R or S or RS form, the resulting ester (I) will normally have the same form.

The esterification reaction can be effected in several ways. In a first method, the reaction is effected with excess alcohol ROH in the presence of a mineral acid catalyst such as e.g. hydrochloric acid. After completion of the reaction, the acid can either be removed by means of an ion exchange resin or simply be neutralized with an organic or inorganic base, whereupon the desired product may be recovered from the reaction mixture by means of chromatographic techniques.

In a second method, the esterification reaction is effected in the presence of an organic activator such as e.g. N,N'-dicyclohexylcarbodiimide. After completion of the reaction, the activator can be inactivated with water whereupon the desired product may be recovered in a conventional way.

The only reaction products of the esterification reaction are esters of formula (I) which may be recovered in sufficiently pure form.

It should be noted that the starting material of the esterification reaction, i.e. the free acid (II) can be prepared along a number of routes. Thus, the acid in (R) or (S) form can be obtained by oxidation of 5-(adenin-9-yl)-5-deoxy aldopentoses, compare A. Holy: Coll.-Czech.Chem.Commun., 43, 3444 (1978). The racemate of the free acid can be obtained in large amounts by successive treatment of adenine with bromacetaldehyde followed by acid hydrolysis, or else by cyanohydrine synthesis followed by acid hydrolysis, compare A. Holy: Coll. Czech. Chem.Commun., 49, 2141 (1984). The free acid is poorly soluble in water and can therefore be efficiently purified.

Further, the free acid could be prepared by adenine ring synthesis, starting from a corresponding amino acid (Jap. Pat. publ. no. 72 04078), by alkylation of adenine with alpha-hydroxypropiolactone (Jap. Pat. publ. no. 72 08549) by reduction of adenine-$N^1$-oxide (Jap. Pat. publ. no. 72 04077) or by alkylation of adenine with activated glyceric acid derivatives (Jap. Pat. publ. no. 72 07550).

The compounds of formula (I) are sufficiently stable in solid state and in neutral solution. Further, they have a good solubility both in aqueous and polar media and in non-polar organic solvents. They have a low acute toxicity for living cells and a non-specific antiviral activity against DNA and RNA viruses. This antiviral activity is especially marked towards vesicular stomatitis viruses and vaccinia virus, although the compounds are also active against measles virus and reovirus type 1. In this broad-spectrum effect, the compounds of formula (I) are similar to DHPA but their level of antiviral activity is higher than that of DHPA.

Pharmaceutical compositions containing compounds of formula (I) as an active ingredient for treating virus diseases in human and veterinary practice may take the form of powders, suspensions, solutions, emulsions, as well as ointments and pastes and may be used for parenteral (intravenous, intradermal, intramuscular, intrathecal, etc.). injections, oral, rectal, vaginal, intranasal administration or topical application (e.g. to lesions of skin, mucosae and eye). Such compositions may be prepared by combining (e.g. mixing, dissolving etc.) the active substance(s) with pharmaceutically acceptable excipients of neutral character (e.g. with aqueous and non-aqueous solvents, stabilisers, emulsifiers, additives), and further, if necessary with dyes and scents. The concentration of the active ingredient in the compositon may vary widely between 0.1 percent and 100 percent, dependent on the character of the disease and the chosen route of administration. Further, the dose of the active ingredient to be administered may vary between 0.1 mg and 1000 mg per kg of body weight.

EXAMPLE 1

The methylester of 3-(adenin-9-yl)-2-hydroxypropanoic acid in (S), (R) and (RS) form as well as the corresponding ethylester in (S) form were prepared according to the following general procedure:

A suspension of (S) or (R) or (RS)-3(adenin-9-yl)-2-hydroxypropanoic acid (5 mmol) in methanol or ethanol (60 ml) was treated with concentrated sulfuric acid (0.6 ml) and the mixture was refluxed under stirring and exclusion of moisture until the reaction (monitored by TLC in a chloroform-methanol mixture, 4:1) was complete, usually after 3–4 h. The mixture was cooled and poured into a suspension of Amberlite IR 45 (50 ml prewashed with dioxane) in dioxane (200 ml). The slurry was stirred for 30 min and filtered; the resin was washed with dioxane (100 ml) and the filtrate evaporated in vacuo to dryness. The residue was chromatographed on two loose-layers (45×16×0.3 cm) of silica in chloroform-methanol mixture (9:1). The products were eluted with methanol (500 ml), the eluate evaporated in vacuo and the residue crystallized from acetone (petrolether added to turbidity) to give the chromatographically pure product.

The resulting methyl and ethyl esters of 3-adenin-9-yl)-2-methoxypropanoi acid had a melting point of 196°–198° C., respectively.

EXAMPLE 2

Several (RS)-3-(adenin-9-yl)-2-hydroxypropanoic acid esters of formula (I) were prepared according to either one of the following general procedures:

Method A. A suspension of (RS)-3-(adenin-9-yl)-2-hydroxypropanoic acid (5mmol) in the corresponding alcohol (60 ml) was treated with concentrated sulfuric acid (0.6 ml) and the mixture was refluxed under stirring and exclusion of moisture till a complete reaction (monitored by TLC in chloroform-methanol mixture, 4:1), usually after 3—4h. The mixture was cooled and poured into a suspension of Amberlite IR 45 (50 ml, prewashed with dioxane) in dioxane (200 ml). The slurry was stirred for 30 min. and filtered; the resin was washed with dioxane (100 ml) and the filtrate was evaporated in vacuo to dryness. The residue was chromatographed on two loose-layers (45×16×0.3 cm) of silica in chloroform-methanol mixture (9:1). The products were eluted with methanol (500 ml), the eluate evaporated in vacuo and the residue crystallized from acetone (petrolether added to turbidity) to give the chromatographically pure products.

Method B. The esterification was performed as indicated in method A. After completion of the reaction, the mixture was cooled with ice and carefully neutralized by triethylamine. The solution was evaporaed to dryness in vacuo, the oily residue dissolved in water (20 ml) and applied immediately onto a column (200 ml) of octadecyl-silica, prewashed with water. The washing with water (6 ml/min) was continued until the eluate showed a drop in conductivity. The column was then washed with a stepwise gradient of aqueous dioxane (5%, 10%, 209%) (1 L each) until the elution of the UV-absorbing compound started. Thereafter, the column was eluted with methanol until the eluate showed a drop in UV-absorption. This eluate was evaporated in vacuo, co-distilled with dioxane (2×50 ml) and the residue was crystallized (acetone/petrolether or dioxane) to afford the chromatographically pure compounds.

Method C. A mixture of (RS)-3-(adenin-9-yl)-2-hydroxypropanoic acid (5 mmol), dimethylformamide (20 ml) and the corresponding alcohol (30 ml) was treated with N,N'-dicyclohexylcarbodiimide (13 mmol) and stirred overnight under the exclusion of moisture at room temperature. Water (100 ml) was added, the suspension filtered and the precipitate washed with water (100 ml). The filtrate was extracted with ether (3×100 ml) and the aqueous phase evaporated in vacuo (finally at 40° C./13 Pa). The residue was redissolved in methanol (50 ml), filtered again and concentrated in vacuo. Further purification was achieved as indicated in method A.

The resulting esters of (RS)-3-(adenin-9-yl)-2-hydroxypropanoic acid and their physical properties are listed in Table I. The Rf values therein have been found by thin-layer-chromatography (TLC) in chloroform-methanol systems, viz. S1 (9:1) and S2 (4:1). With regard to the molecular formulae, the C,H,N analyses correspond to calculated values.

The antiviral properties of the compounds of formula I will now be described in more detail with reference to the following tests.

TEST 1

The antiviral properties of the esters prepared in Example 1 was explored in a variety of cell cultures and with a variety of DNA and RNA viruses such as listed in Table 2. The cells of each cell culture were inoculated with a certain virus in a dose of about 100 $CCID_{50}$, that is about 100 times the dose needed to infect 50 percent of the cells. One hour after inoculation, the celss were washed with Eagle's nutrient medium and an ester of Example 1 was added in a dose varying from zero to 300 ug/ml and sometimes to more than 400 ug/ml. The compound (S)-DHPA was used in a comparative experiment. For each virus-cell system, the minimum inhibitory concentration ($MIC_{50}$) was determined, that is the dose of chemical compound needed to surpress the cytopathic effect of the virus by 50 percent. The cytopathic effect itself was measured in control experiments with virus-infected cell cultures without any added chemical compound and recorded as soon as it reached completion (Method of L. J. Rosenthal and I. L. Schechmaister in "Tissue Culture", p. 510, Academic Press, New York, 1973).

The results are shown in Table 2, wherein the abbreviations have the following meaning: PRK: primary culture of rabbit kidney cells; Vero: continuous line of green monkey kidney cells, HeLa: epithelial line of human cervical carcinoma cells.

It can be derived from Table 2 that the esters of formula (I) are antivirally active against several RNA and DNA viruses and that they have a higher level of activity than (S)-DHPA.

TEST 2

The antiviral properties of the racemic compounds prepared in accordance with Example 2 were explored in the same way as in test 1, using (S)-DHPA and (RS)-DHPA for comparison. The nature of the virus-cell systems and the results are give in Table 3.

It can be derived from Table 3 that the compounds of Table 1 have a remarkable antiviral activity both toward DNA-viruses and RNA-viruses, such as Vaccinia, vesicular stomatitis, parainfluenza, measles and reoviruses. This spectrum of activity is similar to that of (RS) or (S)-DHPA. However, it appears that most of the compounds of Table 1 were about ten times more potent in antiviral activity (towards vesicular stomatitis and vaccinia virus) than DHPA. Such esters were inhibitory to vesicular stomatitis virus and vaccinia virus in concentration ranges of 1-3 ug/ml and 3-10 ug/ml respectively.

TEST 3

A further test was effected to determine the cytotoxicity of the chemical compounds of Table 1. Cell cultures were incubated with varying concentrations of the esters, during a time period equal to the period required for measuring antiviral activity. The compounds (S)-DHPA and (RS)-DHPA were used for comparative purposes. For each compound, the minimum cytotoxic concentration (MCC) was measured, that is the concentration required to cause a microscopically detectable alteration of normal cell morphology, when incubated with the cells in this way. The results are given in Table 4.

It can be derived from Table 4 that the esters from Table 1 were not cytotoxic to the host cells at a concentration below 100 ug/ml. Most of the esters were even devoid of cytotoxicity at a concentration of 400 ug/ml. In view of Table 3, this implies that the antiviral index, as defined by the ratio of the $MIC_{50}$ (toward vesicular stomatitis virus) to the MCC (for PRK cells) was higher than 100-fold for several compounds (Nos. 1,2,4,6,7,8). An antiviral index higher than 400-fold was noted for the racemic ethyl, 2-butyl and 2-methylpropyl esters.

It will be noted from the foregoing test results that the invented esters of formula (I) have an improved antiviral activity towards DNA and RNA viruses, while having a low toxicity for living cells. Thus, these compounds may be used with advantage for treatment of virus diseases in human and veterinary practice.

TABLE 1

| | | Esters of (RS)—3-(adenin-9-yl)-2-hydroxypropanoic acid | | | | | | |
|---|---|---|---|---|---|---|---|---|
| Ester No. | R in Formula (I) | Preparation Method | Yield (%) | M.p. (°C.) | $R_f$ S1 | S2 | Mass spectrum | Mol. formula (mol. weight) |
| 1 | Methyl | A | 68 | 196–198 | 0.15 | 0.37 | 237 | $C_9H_{11}N_5O_3$ (237.2) |
| 2 | Ethyl | A | 65 | 184 | 0.18 | 0.42 | 251 | $C_{10}H_{13}N_5O_3$ (251.2) |
| 3 | 1-Propyl | A | 72 | 164–165 | 0.30 | 0.45 | 265 | $C_{11}H_{15}N_5O_3$ (265.3) |
| 4 | 2-Propyl | B | 80 | 166 | 0.30 | 0.47 | 265 | $C_{11}H_{15}N_5O_3$ |
| 5 | 1-Butyl | A B | 66 84 | 178–179 | 0.42 | 0.62 | 279 | $C_{12}H_{17}N_5O_3$ (279.3) |
| 6 | 2-Butyl | B | 75 | 65–67 | 0.40 | 0.60 | 279 | $C_{12}H_{17}N_5O_3$ |
| 7 | 2-Methylpropyl | B | 80 | 159–160 | 0.42 | 0.60 | 279 | $C_{12}H_{17}N_5O_3$ |
| 8 | 3-Methylbutyl | B | 82 | 139 | 0.55 | 0.70 | 293 | $C_{13}H_{19}N_5O_3$ |
| 9 | 1-Octyl | C | 66 | 136–137 | 0.70 | — | 335 | $C_{16}H_{25}N_5O_3$ (335.4) |
| 10 | 2-Methoxyethyl | A | 70 | 140–141 | 0.32 | 0.46 | 281 | $C_{11}H_{15}N_5O_4$ (281.3) |
| 11 | Cyclohexyl | B | 77 | 178 | 0.57 | 0.70 | 305 | $C_{14}H_{19}N_5O_3$ (305.3) |

TABLE 2

Antiviral activity of compounds of Example 1 in tissue culture

| Virus | Cell type | MIC$_{50}$ (μg/ml) Compound of formula (I), R (configuration) | | | | |
|---|---|---|---|---|---|---|
| | | CH$_3$(S) | CH$_3$(R) | CH$_3$(RS) | C$_2$H$_5$(S) | (S)—DHPA |
| Herpes simplex 1 (KOS) | PRK | >400 | >400 | >400 | >400 | >400 |
| Measles | Vero Flow | 70 | 15 | 40 | 100 | 70 |
| Reovirus 1 | Vero B | 300 | 70 | 300 | 70 | 70 |
| Parainfluenza | Vero B | 100 | 200 | 100 | 100 | 20 |
| Sindbis | Vero B | >400 | >400 | >400 | >400 | >400 |
| Coxsackie B4 | PRK | 150 | 150 | >400 | >400 | 100 |
| Vesicular stomatitis | PRK | 7 | 1.5 | 3 | 1.5 | 30 |
| Vaccinia | PRK | 20 | 15 | 7 | 7 | 70 |
| Polio 1 | HeLa | >400 | >400 | >400 | >400 | >400 |

Antiviral activity of the compounds of Table 1
Minimum inhibitory concentration (μg/ml)

| Compound No. | PRK cells | | | Vero cells | | | | Hela cells | |
|---|---|---|---|---|---|---|---|---|---|
| | Vesicular stomatitis virus | Vaccina virus | Herpes simplex virus-1 (KOS) | Reo virus-1 | Para influenza-virus-3 | Measles virus | Sindbis virus | Coxsackie virus-B4 | Polio virus-1 |
| 1 | 3 | 7 | >400 | 200 | 20 | 40 | >400 | >400 | >400 |
| 2 | 1 | 3 | >400 | 40 | 20 | 20 | >400 | >400 | >400 |
| 3 | 1–3 | 3–10 | >100 | 200 | 100 | 100 | >200 | >400 | >400 |
| 4 | 3 | 3 | >400 | 40 | 70 | 150 | >400 | >400 | >400 |
| 5 | 3 | 3–30 | >200 | 150 | 70 | 25 | 150 | >400 | >400 |
| 6 | 1 | 3 | >400 | 70 | 200 | 40 | 300 | >400 | >400 |
| 7 | 1–3 | 3–30 | >400 | 150 | 20 | 40 | >400 | >400 | >400 |
| 8 | 3 | 10–30 | >400 | 30 | 200 | 12 | 200 | >400 | >400 |
| 9 | 7 | 7 | >100 | 7 | 15 | 70 | 30 | >100 | >100 |
| 10 | 7 | 30 | >400 | 70 | 300 | 400 | >400 | >400 | >400 |
| 11 | 1 | 3 | >100 | 7 | >40 | 15 | >100 | >100 | >100 |
| (S)—DHPA | 15–30 | 30–70 | >400 | 200 | 20 | 30 | >400 | >400 | >400 |
| (RS)—DHPA | 15–30 | 30–70 | >400 | 100 | 20 | 20 | >400 | >400 | >400 |

TABLE 4

Cytotoxic effect of the compounds of Table 1

| Compound no. | Minimum cytotoxic concentration (μg/ml) | | |
|---|---|---|---|
| | PRK | Vero cells | Hela cells |
| 1 | >400 | >400 | >400 |
| 2 | >400 | >400 | >400 |
| 3 | 100 | 400 | 400 |
| 4 | >400 | >400 | >400 |
| 5 | 200 | 200 | 400 |
| 6 | >400 | >400 | >400 |
| 7 | >400 | >400 | >400 |
| 8 | 400 | 400 | 400 |
| 9 | 100 | 200 | 100 |
| 10 | >400 | >400 | >400 |
| 11 | 100 | 100 | 100 |
| (S)—DHPA | >400 | >400 | >400 |
| (RS)—DHPA | >400 | >400 | >400 |

What we claim is:

1. A method for treating virus diseases which comprises administering to a patient in need of said treatment an effective antiviral amount of a 3-(adenin-9-yl)-2-hydroxypropanoic acid ester of the formula (I):

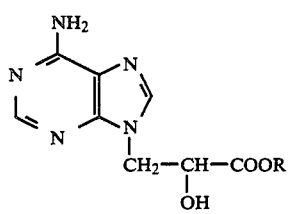

wherein R is linear or branched alkyl with the exception of tert-butyl and n-pentyl, n-octyl, methoxyethyl, or cyclohexyl, in (R), (S), or (RS) form.

2. The method of claim 1, wherein R is methyl.
3. The method of claim 1, wherein R is ethyl.
4. The method of claim 1, wherein R is 1-propyl.
5. The method of claim 1, wherein R is 2-propyl.
6. The method of claim 1, wherein R is 1-butyl.
7. The method of claim 1, wherein R is 2-butyl.
8. The method of claim 1, wherein R is 2-methylpropyl.
9. The method of claim 1, wherein R is 3-methylbutyl.
10. The method of claim 1, wherein R is 1-octyl.
11. The method of claim 1, wherein R is 2-methoxyethyl.
12. The method of claim 1 wherein R is cyclohexyl.
13. The method of claim 1, wherein said virus disease is caused by an RNA virus.
14. The method of claim 1, wherein said virus disease is caused by a DNA virus.
15. The method of claim 1, wherein said virus disease is caused by vesicular stomatitis virus.
16. The method of claim 1, wherein said virus disease is caued by vaccinia virus.
17. The method of claim 1, wherein said virus disease is caused by measles virus.
18. The method of claim 1, wherein said virus disease is caused by reovirus type 1.
19. The method of claim 1, wherein the ester of the formula (I) is administered in the form of a therapeutic composition comprising an effective antiviral amount of the ester of the formula (I) and a pharmaceutically acceptable excipient.
20. The method of claim 1, wherein the ester of the formula (I) is administered in a dose in an amount of between 0.1 mg and 1000 mg per kg of body weight.